(12) United States Patent
Abraham-Fuchs et al.

(10) Patent No.: US 7,585,492 B2
(45) Date of Patent: Sep. 8, 2009

(54) BIOMOLECULAR CONTRAST AGENTS FOR THERAPY SUCCESS AND DOSE MONITORING IN RADIATION THERAPY WITH PROTON OR ION BEAMS

(75) Inventors: Klaus Abraham-Fuchs, Erlangen (DE); Michael Moritz, Mistlegau (DE)

(73) Assignee: Siemens Aktiengesellschaft, Munich (DE)

( * ) Notice: Subject to any disclaimer, the term of this patent is extended or adjusted under 35 U.S.C. 154(b) by 1105 days.

(21) Appl. No.: 10/849,328

(22) Filed: May 18, 2004

(65) Prior Publication Data

US 2005/0260129 A1    Nov. 24, 2005

(51) Int. Cl.
*A61K 49/00* (2006.01)
*A61B 5/00* (2006.01)
*A61B 8/00* (2006.01)

(52) U.S. Cl. .......................................... 424/9.1; 424/9.6

(58) Field of Classification Search ................... 424/9.1
See application file for complete search history.

(56) References Cited

U.S. PATENT DOCUMENTS

| 4,671,256 A | | 6/1987 | Lemelson | |
|---|---|---|---|---|
| 5,813,985 A | | 9/1998 | Carroll | |
| 5,856,673 A | * | 1/1999 | Ikegami et al. | 250/368 |
| 6,083,486 A | | 7/2000 | Weissleder et al. | 424/9.6 |
| 6,217,848 B1 | | 4/2001 | Achilefu et al. | |
| 6,319,682 B1 | * | 11/2001 | Hochman | 435/29 |
| 6,493,570 B1 | | 12/2002 | Dees et al. | |
| 6,761,878 B2 | | 7/2004 | Achilefu et al. | |
| 6,843,980 B2 | * | 1/2005 | Green | 424/9.6 |
| 2001/0022963 A1 | | 9/2001 | Klaveness et al. | |
| 2003/0206611 A1 | | 11/2003 | Collins | |

FOREIGN PATENT DOCUMENTS

| WO | WO 96/23524 A1 | 8/1996 |
|---|---|---|
| WO | WO 99/17809 | 4/1999 |
| WO | WO 00/06244 A3 | 2/2000 |

OTHER PUBLICATIONS

U.S. Appl. No. 10/848,880, Abraham-Fuchs.
U.S. Appl. No. 10/849,267, Abraham-Fuchs.
U.S. Appl. No. 10/848,871, Abraham-Fuchs.

* cited by examiner

*Primary Examiner*—Michael G Hartley
*Assistant Examiner*—Melissa Perreira
(74) *Attorney, Agent, or Firm*—Brinks, Hofer, Gilson & Lione

(57) ABSTRACT

A bio-molecular contrast agent (BMCA) is introduced into a biological organism such that the agent binds or reacts with target tissue within that organism. The BMCA is also signal-giving, and signal reactive, capable of being inactivated by delivery of energy thereto. By monitoring the decrease in signal strength of the BMCA, the actual dosage delivered to the target can be determined and monitored. The decrease in BMCA signal strength can also be correlated to the level of destruction of the target, allowing for determination of therapy success.

24 Claims, 3 Drawing Sheets

BIOMOLECULAR CONTRAST AGENTS FOR THERAPY SUCCESS AND DOSE MONITORING IN RADIATION THERAPY WITH PROTON OR ION BEAMS

CROSS-REFERENCE TO RELATED APPLICATIONS

This application is related to 1) a patent application Ser. No. 10/849,267, entitled "Biomolecular Contrast Agents For Therapy Control In Radiation Therapy With Proton Or Ion Beams", filed concurrently herewith, and incorporated by reference herein; 2) a patent application Ser. No. 10/848,871, entitled "Biomolecular Contrast Agents For Therapy Optimization In Radiation Therapy With Proton Or Ion Beams", filed concurrently herewith and incorporated by reference herein; and 3) a patent application Ser. No. 10/848,880, entitled "Biomolecular Contrast Agents With Multiple Signal Variance For Therapy Planning And Control In Radiation Therapy With Proton Or Ion Beams", filed concurrently herewith and incorporated by reference herein.

BACKGROUND

1. Field of the Invention

This invention relates generally to the art of radiation therapy and diagnostic imaging. More specifically, the invention relates to the use of contrast agents in therapy planning and treatment involved in radiation therapy.

2. Related Art

In the treatment of cancer and other diseases, therapeutic measures such as particle beam therapy are commonly employed. In particle beam therapy, a beam (or beams) of radiation in the form of electrons, or photons, or more recently, protons, is delivered to a tumor or other target tissue. The dosage of radiation delivered is intended to destroy the tumorous cells or tissues.

It is state of the art today that medical imaging techniques such as CT (Computed Tomography), MR (Magnetic Resonance), PET (Positron Emission Tomography), optical imaging (ultraviolet/infrared/visible) or ultrasound are used to visualize the target region (most often a tumor) for particle beam therapy. Yet, the medical imaging techniques used for this purpose in many cases cannot reliably differentiate between malign tumors and benign tumors, and in particular are not well suited to visualize exactly the borderline between healthy tissue and malign tumors. Thus the therapy control methods today are based on non-optimal medical images, and as a consequence, for the sake of a successful destruction of the tumor, the volume to be irradiated usually is chosen larger than absolutely necessary thereby damaging healthy tissue in the process. Exact positioning and dosage is especially critical in therapies that use proton beams, where the energy is highly concentrated in particular locations due to the well-know Bragg Peak phenomenon.

Additionally, it happens in many cases that the images used for therapy planning do not exactly show the location of the target tissue for irradiation during the therapy session, for example because the patient is not positioned exactly in the same way during the imaging and the therapy session, or because the filling of the intestinal tract is different in both sessions, and thus organs are shifted. The composition and relative thickness of fatty tissue, fluids, muscle, and connective tissue in the beam pathway needs to be known, and unfortunately, can change after therapy planning. Recently, artificial or anatomical landmarks are used to control the position of the target tissue.

One solution that has been used recently in some imaging techniques is the introduction of "contrast agents" which enhance the image quality achieved during imaging. To provide diagnostic data, the contrast agent must interfere with the wavelength of radiation used in the imaging, alter the physical properties of the tissue/cell to yield an altered signal or provide the source of radiation itself (as in the case of radiopharmaceuticals). Contrast agents are introduced into the body of the patient in either a non-specific or targeted manner. Non-specific contrast agents diffuse throughout the body such as through the vascular system prior to being metabolized or excreted. Non-specific contrast agents may for instance be distributed through the bloodstream and provide contrast for a tumor with increased vascularization and thus increased blood uptake. Targeted agents bind to or have a specific physical/chemical affinity for particular types of cells, tissues, organs or body compartments, and thus can be more reliable in identifying the correct regions of interest.

Several different targeted contrast agents which bind to particular tissue and then exhibit signal changes based upon state changes in tissues (which are then imaged) are disclosed in international patent application WO 99/17809, entitled "Contrast-Enhanced Diagnostic Imaging Method for Monitoring Interventional Therapies".

In particular, the dosage of energy that is planned for can often not be measured, determined or monitored very accurately. Further, even if the planned dosage of energy is delivered to a target tissue, it is not usually known until after treatment whether the treatment succeeded in destroying the target tissue.

The methods used today in monitoring of dosage and success in radiation therapy a in real-time during the therapy session, are sub-optimal and need to be improved.

DETAILED DESCRIPTION OF THE INVENTION

Figure 1:
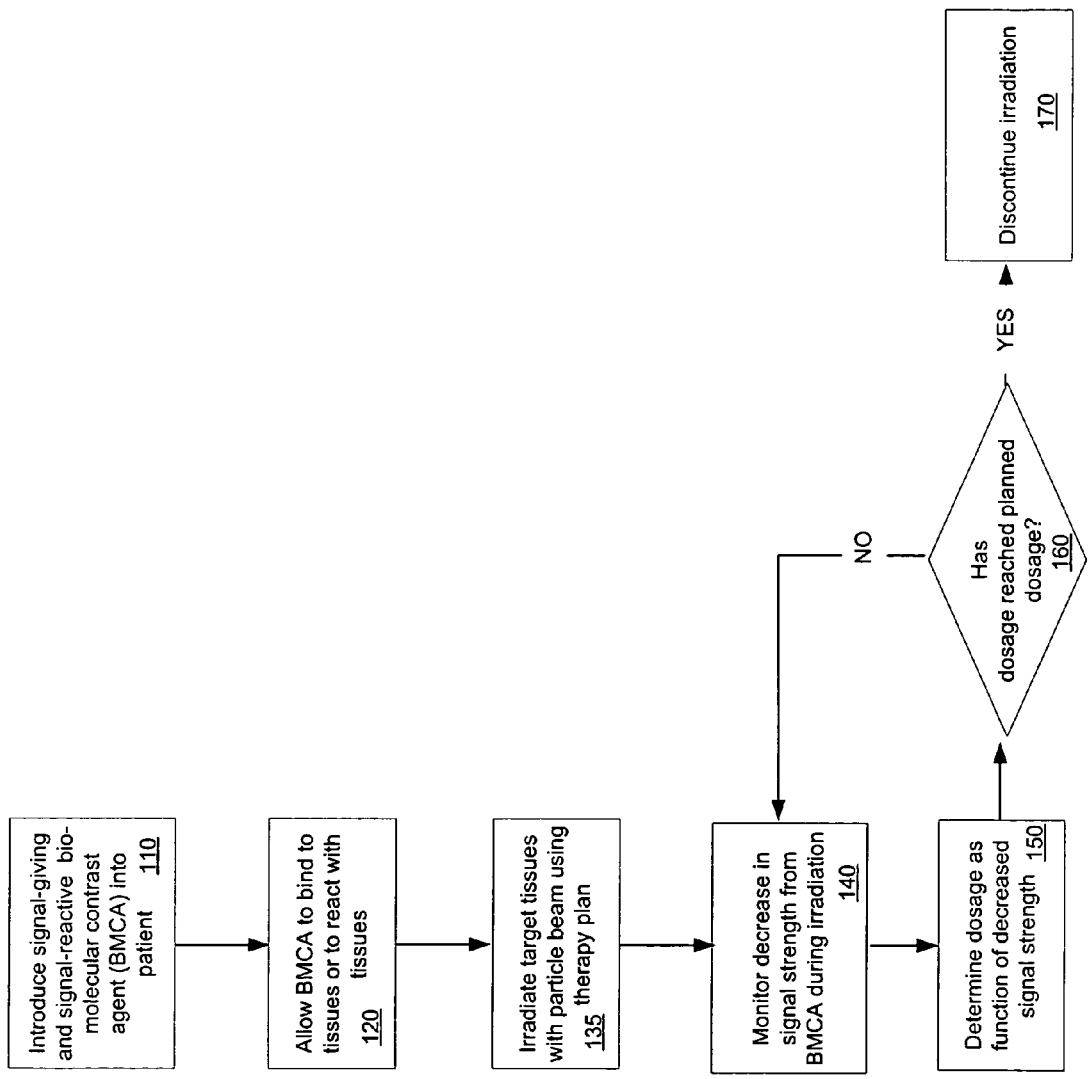
FIG. 1 illustrates one embodiment of the invention wherein dosage monitoring is performed using BMCA.

In various aspects of the invention, bio-molecular contrast agents (BMCAS) are introduced into a patient for the purpose of radiation therapy planning and treatment. "BMCA", as the term is used in describing this invention, are at least partially organic contrast agents which have the following properties: 1) they bind to target tissue, cells, and organs, and/or (2) react with metabolic products of the target tissue, cells, and organs by means of highly specific biochemical reactions (such as body-anti-body mechanisms). This yields an improved highly precise image of the target region for irradiation. In some embodiments, the invention also uses BMCA that are designed to have certain signal-giving properties as well as having a binding or reactive function. The reactive function can also activate the signal-giving property of the BMCA. These mechanisms help to ensure that the signals used for therapy planning, monitoring and control originate only from the target tissue.

For instance, fluorescent BMCAs, such as the ones described in U.S. Pat. No. 6,083,486, can be used in conjunction with a medical optical imager, like an optical tomograph or a diaphanoscope. Some embodiments may also or alternatively employ luminescent and/or phosphorescent BMCAs.

As illustrated by the invention such BMCAs and other BMCAs can be adapted for use in therapy planning and real-time, on-line therapy control. One advantage of such BMCAs over conventional contrast agents is that the BMCAs stay immobilized for a longer period within the target tissue, due to the highly specific and stable binding reaction. Thus BMCAs are available for a longer time period to observe/monitor the target region than are conventional contrast agents.

BMCAs can also be designed or selected such that their signal-giving property diminishes when the BMCA interacts with the particle beam. The BMCA can thus be "inactivated" (with respect to its signal-giving property) through irradiation with a particle beam of enough energy. For instance, a fluorescent contrast agent may be inactivated by destroying the fluorescence property of the BMCA which would involve breaking of the functional covalent C-C and/or C-H bindings of the BMCA through irradiation. In some embodiments of the invention, the beam energy, or respectively the irradiation dose, needed to inactivate the signal-giving property of the BMCA is roughly the same energy or dose as needed for successful medical treatment of the target tissue.

In this way, two types of information can be derived from the BMCA: the presence of the BMCA through specific binding indicates the target region for treatment. Subsequent diminishing of the signal by destroyed signal-giving properties of the BMCA through the particle beam indicate that the target region has successfully been treated with the particle beam.

If the BMCA is designed/selected such that the decrease in signal from the contrast agent due to irradiation is roughly proportional to the dosage of radiation being delivered, then the BMCA can be used as a dosage monitoring and therapy success mechanism. However, the signal of the BMCA must not decline at a rate that is much faster or much slower than the increase in radiation dose such that a usable reading is not possible. In other words, if the signal diminishes too rapidly or too slowly with increasing irradiation, then the BMCA would lose its effectiveness as a dosage/therapy monitoring mechanism.

It is especially advantageous for the purpose of therapy success monitoring/control if the BMCA is designed such that the irradiation dose necessary to inactivate the BMCA corresponds roughly to the dose necessary to destroy DNA material in the target. Destruction of DNA material is one of the most important known mechanisms in the destruction of tumors through particle irradiation. In such a case, it can be assumed that the decrease of signal from the BMCA by interaction with particle beam is proportional to the degree of destruction of the tumor. To achieve this, in accordance with the invention, the BMCA is designed such that, in order to inactivate the signal-giving property of the BMCA, the destruction of one or more functional covalent C-C and/or C-H bindings (in the DNA) is necessary.

BMCA include small molecules and preferably bio-molecules with an affinity or reactivity with the target tissue. The affinity to bind or reactivity can be dependent on tissue state or tissue type or both. Bio-molecules are typically biologically derived or synthesized from naturally occurring elements such as amino acids, peptides, nucleotides and so on. Examples include receptor ligands, saccharides, lipids, nucleic acids, proteins, naturally occurring or genetically engineered anti-bodies. BMCA include those bio-molecules which can bind to proteins in plasma, in the fluid between cells, or in the space between cells. BMCA also includes dyes and other signal generating compounds, as desired. The difference in binding affinity of one bio-molecule versus another can have an effect in the signals that are ultimately received from the BMCA and in the accuracy of the binding to the target tissues. Thus, the specific nature and structure of the BMCA selected for the purpose of therapy control will depend upon which tissue or tissue component is to be bound. The binding sites for BMCA include such components and tissue as bones, calcified tissues, cancerous tissues, cell membranes, enzymes, fat, certain fluids (such as spinal fluid), proteins etc. BMCAs used in this invention may also include pharmaceutically accepted salts, esters, and derived compounds thereof, including any organic or inorganic acids or bases. BMCA may be accompanied by other agents, such as salts, oils, fats, waxes, emulsifiers, starches, wetting agents which may be used to aid in carrying the BMCAs to the target more rapidly or more securely, or in diffusing the BMCAs into external tissue such as skin.

In one embodiment of the invention, the dosage that is actually being delivered to the target tissue by means of the particle therapy system can be measured and monitored by the use of BMCAs. The BMCAs have the functionality of binding to tissue but of also having a signal-giving property which is destroyed in whole or part by the irradiation of the particle beam in a manner proportional with the dosage of irradiative energy delivered to the target. The BMCAs are introduced into the body of the patient and allowed to bind to the target tissues. The particle beam then irradiates the target tissue. During irradiation, the strength of the signal from the BMCA is sensed and monitored. A decrease in signal strength from the BMCA is then associated with a particular delivered dosage of radiation. Once the desired dosage is achieved, irradiation in that area is discontinued.

FIG. 1 illustrates dose monitoring in accordance with at least one embodiment of the invention. A bio-molecular contrast agent or agents (BMCA) is introduced into the patient or animal or other organism being treated (block 110). Methods for introduction of BMCA may be similar to methods used to introduce other contrast agents, such as intravenous or oral and may be targeted or non-specific (such as those which spread throughout a region of the body). Other methods specific to BMCA may also be used. The BMCA, once introduced, is allowed to bind to tissues or react with the tissues (block 120). Thus, a suitable delay after introduction of the BMCA is required. This delay will vary based upon the type of binding or reaction, the type, size and location of the target tissue, the characteristics/affinity of the BMCA, and so on. The time for allowance should be sufficient to stabilize the BMCA binding or reaction with the target.

The BMCAs introduced according to block 110 are also "signal-reactive" in that the strength of signal diminishes with an increasing dose of radiation. This diminution of signal can be proportional to the increase in dosage. Alternatively, the BMCA can be designed/selected such that the signal diminishes to zero or almost zero (to an indistinguishable or sensor indistinguishable level) when the desired dosage of radiation is reached. If the proportionality is linear, the ratio of decrease in signal strength of the BMCA compared to the increase in dosage of radiation should not be too high. A very high ratio would not give meaningful results in terms of measuring dosage. Similarly a very low ratio would not give meaningful results as minute changes in signal may not be able to interpreted accurately. Therefore, in a preferred embodiment of the invention, the rate of decrease in BMCA signal strength and rate of increase in dosage is roughly equal.

Next, the target tissues are irradiated with the particle/radiation beam (block 135) which may include any form of radiation including particle beams comprised of one or more of protons, electrons and photons. During irradiation, the strength of the signal from the BMCA is monitored continuously or at defined intervals (block 140). This monitoring may be performed by manual and/or automated means. In either case, a detection/sensing system would capture the strength of the signal and convert this into a value which can be fed to a dosage monitoring engine. The dosage monitoring engine may include a look-up table or a computational engine which utilizes the signal strength as a parameter of a pre-programmed or hardwired algorithmic function. Using this engine, the level of dosage already delivered to the target can be determined (block 150). Preferably, the dosage determination itself is automated. The determined dosage is compared to a planned dosage level given by the therapy plan and/or to expected dosage level given by dosimetric computation or similar modeling (block 160). Irradiation by the particle beam continues until the determined dosage has reached the planned level. Once it does, irradiation is discontinued (block 170).

The process flow of FIG. 1 is repeated for every position of the particle beam which targets a particular region of the target. Once irradiation is discontinued at region of the target, it is repeated in other regions of the target until the target is exposed to the dosage determined in accordance with the therapy plan. Dosage monitoring can be used in variety of applications other than therapy such as in testing and calibration of the particle beam delivery system. The use of BMCA as a dosage monitoring mechanism can be more relevant than conventional dosage monitoring (which measures dosage in arbitrary volume of any tissue) since only the target tissue (to which the BMCA is bound) is being irradiated as well as measured. With a BMCA signal which corresponds well with radiation dosage, the actual radiation delivered to the target is measurable, rather than the estimated or perceived dosage. For instance, if there are unknown impediments in the beam path prior to reaching the target tissue, such impediments could be recognized by failure of the BMCA signal to inactivate, or to inactivate more slowly than expected in response to a delivered dose.

Figure 2:
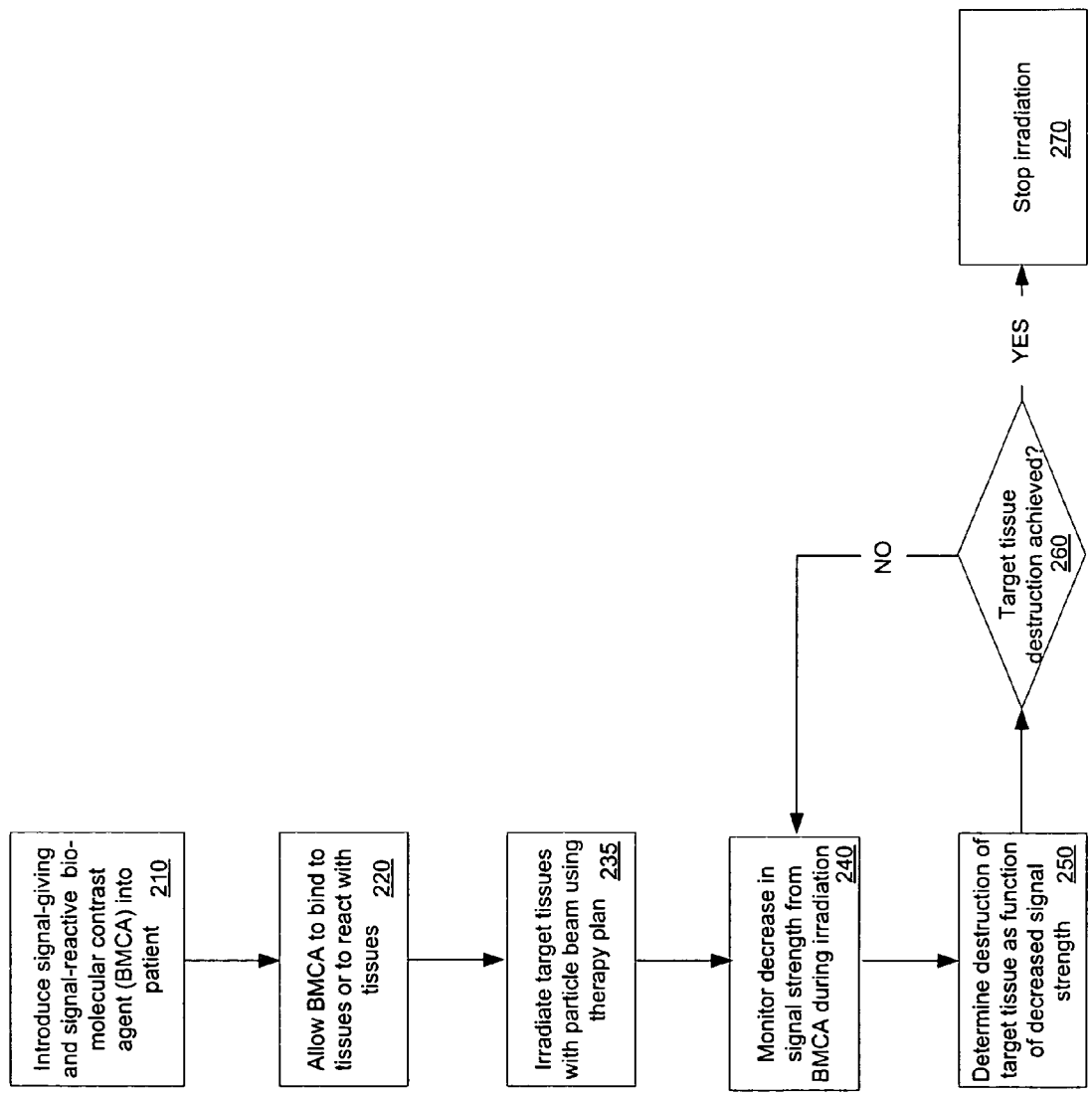
FIG. 2 illustrates one embodiment of the invention wherein therapy success is determined using BMCA.

FIG. 2 illustrates one embodiment of the invention wherein therapy success is determined using BMCA. While dosage monitoring can be a useful tool, it would only tend to demonstrate what dosage has been delivered to the target, or allow the planned dosage to be delivered. Strictly speaking, it may or not be an indicator of the success of the particle therapy. In the case of tumorous tissue, for instance, the goal is destruction of the tissue through particle beam irradiation. While an estimate of the dosage required to destroy the tissue can be obtained in pre-therapy planning session, it is only an estimate and not a guarantee of success. In accordance with the invention, a method and system of monitoring and determining the success of therapy is disclosed which utilizes particular type of BMCA.

A bio-molecular contrast agent or agents (BMCA) is introduced into the patient or animal or other organism being treated (block 210). Methods for introduction of BMCA may be similar to methods used to introduce other contrast agents, such as intravenous or oral and may be targeted or non-specific (such as those which spread throughout a region of the body). Other methods specific to BMCA may also be used. The BMCA, once introduced, is allowed to bind to tissues or react with the tissues (block 220). Thus, a suitable delay after introduction of the BMCA is required. This delay will vary based upon the type of binding or reaction, the type, size and location of the target tissue, the characteristics/affinity of the BMCA, and so on. The time for allowance should be sufficient to stabilize the BMCA binding or reaction with the target.

The BMCA selected/designed for introduction according to block 220 is also "signal-reactive" and moreover corresponds with the destruction of the DNA material constituting the target. The dose required to inactivate the BMCA signal roughly corresponds to the dose needed to destroy DNA material (and hence breakdown or destroy the target tissue or cells). Destruction of DNA material is one of the most important known mechanisms in the destruction of tumors through particle irradiation. In such a case, it can be assumed that the decrease of signal from the BMCA by interaction with particle beam is proportional to the degree of destruction of the tumor. To achieve this, in accordance with the invention, the BMCA is designed such that, in order to inactivate the signal-giving property of the BMCA, the destruction of one or more functional covalent C-C and/or C-H bindings (in the DNA) is necessary.

Next, the target tissues are irradiated with the particle/radiation beam (block 235) which may include any form of radiation including particle beams comprised of one or more of protons, electrons and photons. During irradiation, the strength of the signal from the BMCA is monitored continuously or at defined intervals (block 240). This monitoring may be performed by manual and/or automated means. In either case, a detection/sensing system would capture the strength of the signal and convert this into a value which can be correlated to the degree of destruction of the DNA in the target. The correlation may be performed by use of a look-up table or a computational engine which utilizes the signal strength as a parameter of a pre-programmed or hardwired algorithmic function to obtain the level of DNA destruction. Using this the level of destruction of the target can be determined (block 250). Preferably, this determination itself is automated. Irradiation by the particle beam continues until it has been determined that the tumor has been destroyed (checked at block 260). Once it does, irradiation is discontinued (block 270).

The process of therapy success monitoring enables the exact dosage of radiation to be delivered and no more or no less, and thus allows deviation from the therapy plan. It ensues that irradiation is ceased when the therapy has been deemed successful (when the tissue is determined to be destroyed). Unlike conventional means, therapy success is monitored in a real time fashion without the need of an external imaging system to visualize the tumor. Further, it enhances the quality of the therapy session by reducing the likelihood that a post-treatment phase analysis of the target will yield an unwanted result (i.e. that the tumor was no in fact destroyed).

Figure 3:
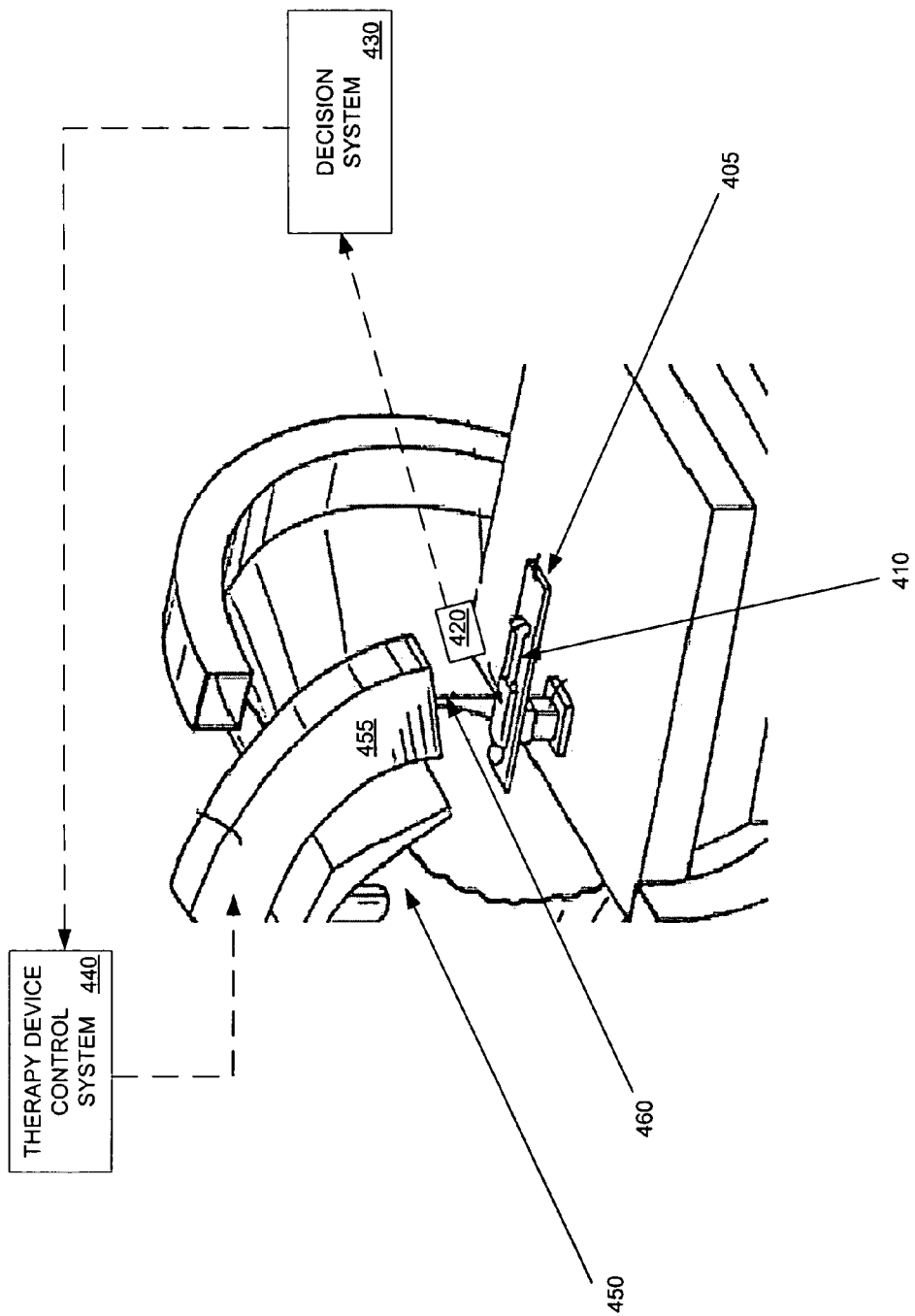
FIG. 3 illustrates a system utilizing one or more embodiments of the invention.

FIG. 3 illustrates a system utilizing one or more embodiments of the invention. At least a portion of a treatment room 400 is shown which houses a therapy device 450 and bed 405 which positions a patient 410 for treatment by treatment device 450. Treatment device 450 may be a radiation or energy delivery system such as proton or photon particle beam delivery system. Treatment device 450 may include a gantry (pictured but not enumerated) and treatment head 455. Treatment head 455 is responsible primarily for delivering and directing the desired or planned energy to patient 410 in the form of a beam 460, for instance. Treatment head 455 may include a number of different elements include scattering elements, collimators, boluses, refraction/reflection elements, and so on.

Generally, in the case of a beam 460 which is composed of particles (such as photons, protons, electrons, neutrons and heavy ions), a particle stream is externally generated and accelerated (by a cyclotron and/or linear accelerator) and then the particle stream (or a portion of it) is delivered to treatment head 455. Treatment head 455 can limit or define both the size and shape of the beam 460 as well as the intensity of the beam 460. Treatment head 455 may also contain a nozzle which can be rotated in different axes to deliver the beam 460. Utilizing this nozzle and various elements within the treatment head 455, therapy device 450 can deliver energy into patient 410 at a different incident angle and with varying shape, size and intensity, as desired. A therapy device control system 440 may be employed for the purpose of controlling the various elements of the treatment head 455 and for controlling the level of energy (dosage) introduced from the externally generated particle source.

In accordance with the invention, prior to treatment by treatment device 450, a BMCA is introduced into patient 410. The BMCA is given time to bind or react to target tissue within the patient 410 to which the beam 460 is to be directed. As mentioned earlier, the target tissues can be initially located using an imaging technique or body marking or similar technique either currently or previously by way of a therapy planning session. The therapy device control system 440 utilizes this initial location information to direct beam 460 towards patient 410. This begins irradiation of the target tissue.

During irradiation, the geometry and location of the target tissue can be tracked by a sensing system 420. Sensing system 420 will be capable of receiving or detecting the signal emitted by the signal-giving property of the BMCA which is bound to the target tissue within patient 410. Sensing system 420 may be, for example, an optical tomography device or a diaphonoscope which can detect the fluorescence given off the BMCA. The signals emitted by the BMCA may be optical, ultraviolet, infrared, electromagnetic (in the case of a radio-pharmaceutical BMCA), and so on. Sensing system 420 will be designed/selected in order to detect this signal and transfer this sensor data to decision system 430. Sensing system 420 may also include a source (not pictured) such as X-ray source in the case of simple X-ray imaging. Sensing system 420 will be able detect the presence and strength of the BMCA signal emitted from patient 410, and responding thereto, generate data which can be utilized in determining the dosage delivered to or the level of destruction of the target tissue to which the BMCA is bound. While sensing system 420 is pictured as a non-integrated unit, it can be integrated with the treatment head 455, if desirable, or positioned or integrated anywhere on the therapy device 450 as appropriate.

In some embodiments of the invention, the BMCA signal can be inactivated by exposure to beam 460. In such instances, the sensing system will detect the strength of the BMCA signal as an indication of impaction of beam 460 with the target. In response to data received from sensing system 460, decision system 430 will be able to determine the dosage delivered to the target tissue. In yet other embodiments of the invention, the BMCA signal strength can be correlated with the level of destruction of the target tissue, and thus used measure the level of therapy success. Decision system 430 may also have access to a pre-therapy image or images of the target tissue for comparison. Decision system 430 will determine if the therapy device has delivered the needed dosage to patient 410. If it has, then decision system 430 can indicate this to the therapy device control system 440. The therapy device control system 440 can change the direction or angle of the beam 460 to redirect the beam 460 to a different area which has not been given the needed dosage or terminate the beam altogether. In other embodiments, the beam 460 can also be re-targeted or stopped altogether, if necessary, particularly if the sensing system 420 and decision system 430 indicates that the target tissue has been destroyed. The decision system 430 may send dosage level information which can then be manually evaluated by an operator handling therapy device control system 440, or the action by the therapy device control system 440 can be automated, whichever is more desired. Decision system 430 will be configured to determine the dosage level or destruction level of the tumor based upon correlating the BMCA signal strength thereto.

The systems mentioned in the above description including the sensing system 420, decision system 430 and therapy device control system 440 may be any combination of hardware, software, firmware and the like. Further, all of these systems may be integrated onto the same hardware platform or exist as software modules in a computer system or both. The systems may be distributed in a networked environment as well and may be stand-alone components. One or more of the systems 420, 430 and 440 may be integrated with the therapy device 450 itself, or separate therefrom. Further, any number of these systems 420, 430 and 440 may be physically separated from the therapy device and manually/automatically monitored or controlled. Systems 420, 430 and 440 may utilize or be loaded into processors, storage devices, memories, network devices, communication devices and the like as desired. Sensing system 420 may also contain cameras, sensors, and other active/passive detection and data conversion components, without limitation. For instance, tables correlating BMCA signal strength to dosage levels can be stored in one ore more of these systems or externally made available to decision system 430.

While the embodiments of the invention are illustrated in which it is primarily incorporated within a radiation therapy system, almost any type of medical treatment of imaging system may be potential applications for these embodiments. Further, the bio-molecular contrast agents used in various embodiments may be any organic or semi-organic compounds which have the desired effect of affinity to certain target tissues/cells to either bind with them or react with them. The examples provided are merely illustrative and not intended to be limiting.

What is claimed is:

1. A method for determining an actual dosage of energy delivered from an energy delivery system to a target, said target within a biological organism, said method comprising:
   introducing a bio-molecular contrast agent (BMCA) into said biological organism, said BMCA capable of at least one of binding to said target and reacting with said target, said BMCA also emitting signals, said signals capable of being inactivated by interacting with said energy;
   directing said energy delivery system to deliver energy to said target after said BMCA has bound or reacted to said target; and
   during delivery, determining said actual dosage based on BMCA signals originating from said target.

2. A method according to claim 1 further comprising: detecting said BMCA signals originating from said target.

3. A method according to claim 2 further comprising: comparing said determined actual dosage with a planned or expected dosage.

4. A method according to claim 3 further comprising:
   discontinuing delivery of energy to said target if said determined actual dosage at least nearly equals said planned or expected dosage.

5. A method according to claim 1 wherein said target comprises a tissue in a particular state.

6. A method according to claim 1 wherein said energy delivery system is a particle beam therapy system.

7. A method according to claim 3 wherein said detecting is performed using a signal capture mechanism.

8. A method according to claim 7 wherein said detecting comprises sensing of emitted radiation.

9. A method according to claim 1 wherein said BMCA signals include at least one of fluorescence, luminescence and phosphorescence.

10. A method according to claim 8 wherein said emitted radiation includes at least one of visible, infrared and ultraviolet light.

11. A method according to claim 1 wherein said the energy delivery system delivers at least one of proton, photon, heavy ion, neutron and electron particles.

12. A method according to claim 1 wherein said actual dosage is roughly proportional to a decrease in strength of BMCA signals.

13. A method for determining destruction of a target by delivery of energy from an energy delivery system, said target within a biological organism, said method comprising:

introducing a bio-molecular contrast agent (BMCA) into said biological organism, said BMCA capable of at least one of binding to said target and reacting with said target, said BMCA also emitting signals, said signals capable of being inactivated by interacting with said energy;

directing said energy delivery system to deliver energy to said target after said BMCA has bound or reacted to said target; and during delivery, determining a level of destruction of DNA in said target based on BMCA signals originating from said target.

14. A method according to claim 13 further comprising: detecting said BMCA signals originating from said target.

15. A method according to claim 13 further comprising: correlating said level of destruction of DNA to a measure of therapy success.

16. A method according to claim 15, further comprising: discontinuing delivery of energy to said target if therapy is determined successful.

17. A method according to claim 13 wherein said target comprises a tissue in a particular state.

18. A method according to claim 13 wherein said energy delivery system is a particle beam therapy system.

19. A method according to claim 14 wherein said detecting is performed using a signal capture mechanism.

20. A method according to claim 19 wherein said detecting comprises sensing of emitted radiation.

21. A method according to claim 13 wherein said BMCA signals include at least one of fluorescence, luminescence and phosphorescence.

22. A method according to claim 20 wherein said emitted radiation includes at least one of visible, infrared and ultraviolet light.

23. A method according to claim 13 wherein said the energy delivery system delivers at least one of proton, photon, heavy ion, neutron and electron particles.

24. A method according to claim 13 wherein the level of destruction of DNA in the target is roughly proportional to a decrease in strength of BMCA signals.

* * * * *